United States Patent [19]

Gordon et al.

[11] 4,337,197
[45] Jun. 29, 1982

[54] O-SULFATED β-LACTAM HYDROXAMIC ACIDS AND INTERMEDIATES

[75] Inventors: Eric M. Gordon, Pennington; Miguel A. Ondetti, Princeton, both of N.J.

[73] Assignee: E. R. Squibb & Sons, Inc., Princeton, N.J.

[21] Appl. No.: 202,830

[22] Filed: Oct. 31, 1980

[51] Int. Cl.³ ............... C07D 205/08; A61K 31/395; C07D 403/12; C07D 409/12
[52] U.S. Cl. .......................... 260/239 A; 260/245.4; 260/330.3; 260/330.9; 424/244; 562/567; 562/579; 564/152; 544/359; 546/275
[58] Field of Search ................................. 260/239 A

[56] References Cited

U.S. PATENT DOCUMENTS

| 3,278,523 | 10/1966 | Blener | 260/239 A |
| 3,297,683 | 1/1967 | Blener | 260/239 A |
| 3,663,535 | 5/1972 | Beattman | 260/239 A |
| 3,816,408 | 6/1974 | Gladycl | 260/239 A |
| 3,855,348 | 12/1974 | Pautrad | 260/239 A |
| 4,068,075 | 1/1978 | Menard | 260/239 A |
| 4,071,512 | 1/1978 | Wolfe | 260/239 A |

FOREIGN PATENT DOCUMENTS

| 846934 | 4/1977 | Belgium . |
| 849445 | 6/1977 | Belgium . |
| 2747494 | 5/1978 | Fed. Rep. of Germany . |
| 49-66813 | 6/1974 | Japan . |
| 1519495 | 7/1978 | United Kingdom . |
| 2000768 | 1/1979 | United Kingdom . |
| 2008574 | 6/1979 | United Kingdom . |

OTHER PUBLICATIONS

Mattingly et al., J. Amer. Chem. Soc. 101, 3983-3985 (1979).
Nicolas et al., Gazz Ital. Chim. 93, 618 (1963).
Taylor et al., Biochem. Biophys. Acta. 286, 107 (1972).
Steward et al., Nature 229, 174 (1971).
Scannell, J. Antibiotics 28, 1, (1975).
Durbin et al., Phytochemistry 17, 147 (1978).
Lahaus, Berichte 105, 2791 (1972).
Drey et al., J.C.S. Perkins I, 1973, 2001.
Mattingly et al., J. Amer. Chem. Soc. 101, 3983-3985 (1979).
Hashimoto, J. Antibiotics 29, 890 (1976).
Lattrell, Ann. Chem. 722, 132 (1969).
Graf et al., Ang. Chem. Int. Ed. 7, 172, (1968).
Miller et al., J. Org. Chem. 42, 1750 (1977).

Primary Examiner—Mark L. Berch
Attorney, Agent, or Firm—Lawrence S. Levinson; Donald J. Barrack

[57] ABSTRACT

Antibacterial activity is exhibited by β-lactams having a sulfate substituent in the 1-position and an acylamino substituent in the 3-position.

1 Claim, No Drawings

O-SULFATED β-LACTAM HYDROXAMIC ACIDS AND INTERMEDIATES

RELATED APPLICATION

United States patent application Ser. No. 188,893, filed Sept. 29, 1980, ABN discloses β-lactam antibiotics having a sulfonic acid salt (SO$_3^\ominus$M$^\oplus$) substituent in the 1-position and an acylamino substituent in the 3-position.

BACKGROUND OF THE INVENTION

The β-lactam ring,

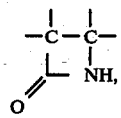

has been known since the late nineteenth century. While knowledge of β-lactam chemistry developed during the early 1900's, it was not until 1929 that Fleming reported in *Brit. J. Exper. Pathol.*, 10, 226 (1929) that a fermentation product of the organism *Penicillium notatum* had antibiotic properties. The compound which Fleming had worked with was benzylpencillin,

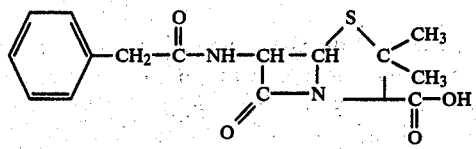

The in vivo activity of benzylpenicillin against various bacteria was reported by Chain et al. in Lancet, 2:226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid,

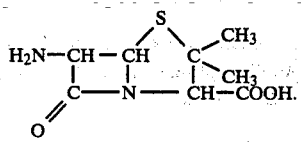

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalosporin C,

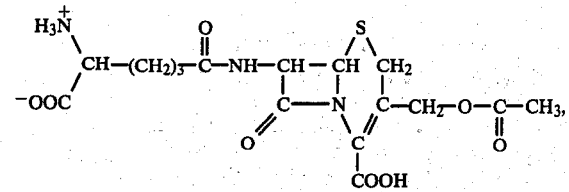

proved to be an important stepping stone in cephalosporin research. Removal of the acyl group in the 7-position of cephalosporin C yields 7-aminocephalosporanic acid,

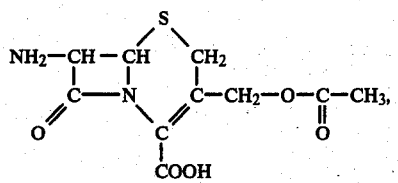

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3):122 (1972) disclose that certain actinomycete cultures isolated from soil produce antibiotics characterized by a methoxy group and D-α-aminoadipic acid on the 7-carbon of the cephem nucleus. The cephamycins, as they are known, have the formula

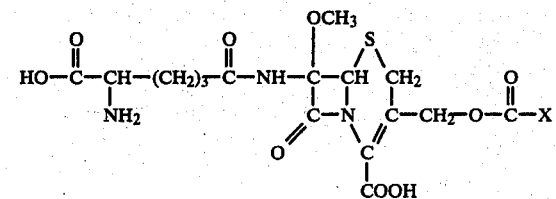

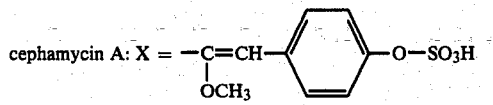

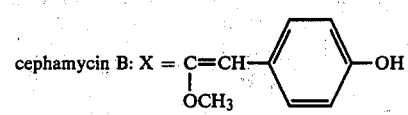

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., *The Journal of Antibiotics*, XXVIII(1):1 (1975), disclose the isolation from a fermentation broth of Streptomyces species 372A of (S)-alanyl-3-[α-(S)-chloro-3-(S)-hydroxy-2-oxo-3-azetidinyl-methyl]-(S)-alanine, which has the formula

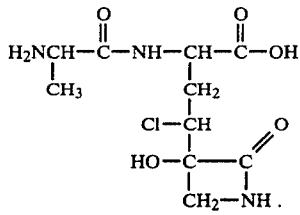

The structure of the above naturally occurring monocyclic β-lactam containing molecule is similar to the structure of the earlier discovered β-lactam containing molecules known as tabotoxins, i.e.,

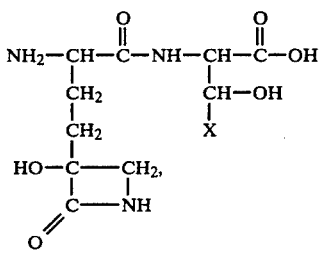

wherein X is hydrogen or methyl as reported by Stewart, Nature, 229:174 (1971), and Taylor et al., Biochem. Biophys. Acta., 286:107 (1972).

Recently, several novel series of naturally occurring β-lactam antibiotics have been isolated. The nocardicins, nocardin A and B, are monocyclic β-lactams having the formula

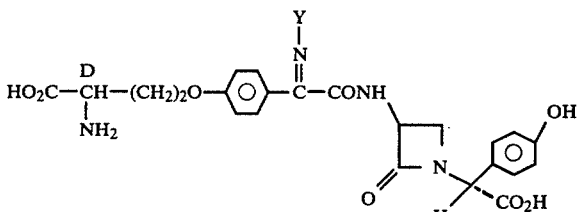

nocardicin A: Y = —syn(Z)OH nocardicin B: Y = —anti(E)OH, as reported by Hashimoto et al., The Journal of Antibiotics, XXIX (9):890 (1976).

Clavulanic acid, a bicyclic β-lactam antibiotic isolated from fermentation broths of Streptomyces clavuligerus, has the formula

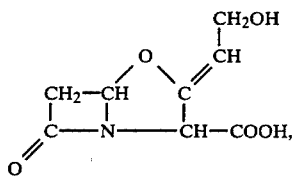

i.e., Z-(2R, 5R)-3-(β-hydroxyethylidene)-7-oxo-4-oxa-1-azabicyclo[3,2,0]heptane-2-carboxylic acid, as reported by Lloyd et al., J.C.S. Chem. Comm., 266 (1976).

Still another recently isolated β-lactam antibiotic is thienamycin, an antibiotic isolated from the fermentation broths of Streptomyces cattleya. As reported by Albers-Schonberg et al., J.A.C.S., 100:20, 6491 (1978), thienamycin has the structure

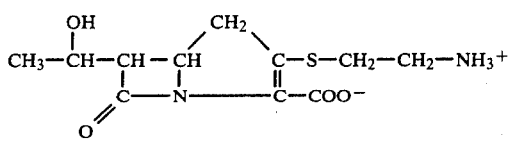

Additional fused β-lactams, olivanic acid derivatives, have recently been isolated from cultures of Streptomyces olivaceus. As disclosed by Brown et al., J.C.S. Chem.Comm., these olivanic acid derivatives have the formulas

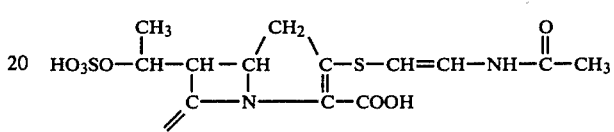

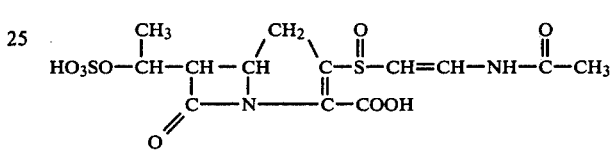

The isolation of the above antibiotics, and a discussion of their activity, is reported by Butterworth et al., The Journal of Antibiotics, XXXII(4):294 (1979) and by Hood et al., The Journal of Antibiotics, XXXII(4):295 (1979).

Another recently isolated β-lactam antibiotic is PS-5, reported by Okamura et al., The Journal of Antibiotics, XXXI: 480 (1978) and The Journal of Antibiotics, XXXII(4):262 (1979). The structure of this antibiotic, which is produced by Streptomyces cremeus subspecies auratilis, is reported to be

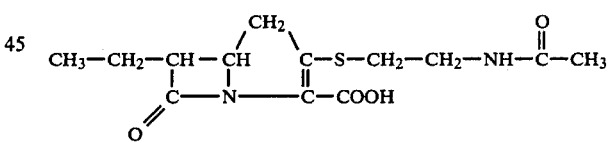

Structurally related antibiotics PS-6 and PS-7 are reported in European Patent Application Ser. No. 1,567 to have the respective structures

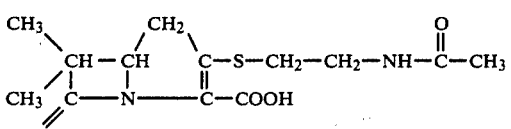

and

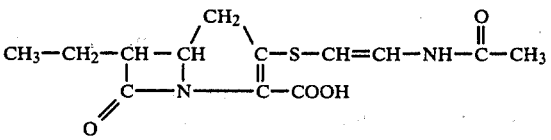

BRIEF DESCRIPTION OF THE INVENTION

This invention is directed to a novel family of β-lactam antibiotics, and to the use of such compounds as antibacterial agents. It has been discovered that the β-lactam nucleus can be biologically activated by a sulfate (—O—SO$_3$⊖M⊕) substituent attached to the nitrogen atom in the nucleus.

β-Lactams having a sulfate substituent in the 1-position and an acylamino substituent in the 3-position exhibit activity against a range of gram-negative and gram-positive bacteria.

The preferred members of the novel family of β-lactam antibiotics of this invention are those encompassed by the formula

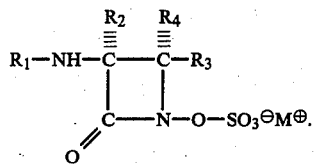

In addition to the above described β-lactams having a sulfate substituent in the 1-position and an acylamino substituent in the 3-position, this invention also encompasses β-lactams having a sulfate substituent in the 1-position and an amino (NH$_2$) substituent in the 3-position. The preferred compounds of this type have the formula

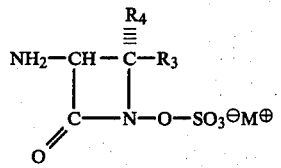

These compounds are intermediates useful for the preparation of corresponding 3-acylamino compounds.

As used in formulas I and Ia, and throughout the specification, the symbols are as defined below.

R$_1$ is acyl;
R$_2$ is hydrogen or alkoxy of 1 to 4 carbons;
R$_3$ and R$_4$ are the same or different and each is hydrogen or alkyl; and
M⊕ is hydrogen or a cation, with the proviso that if M⊕ is hydrogen the 3-substituent contains a basic function.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "alkenyl" refers to both straight and branched chain groups. Those groups having 2 to 10 carbon atoms are preferred.

The term "halogen" refers to fluorine, chlorine, bromine and iodine.

The term "protected carboxyl" refers to a carboxyl group which has been esterified with a conventional ester protecting group. These groups are well known in the art; see, for example, U.S. Pat. No. 4,144,333, issued Mar. 13, 1979. The preferred protected carboxyl groups are benzyl, benzhydryl and t-butyl esters.

The term "acyl" includes all organic radicals derived from an organic acid (i.e., a carboxylic acid) by removal of the hydroxyl group. Certain acyl groups are, of course, preferred, but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677 published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 17, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_5$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

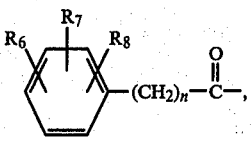

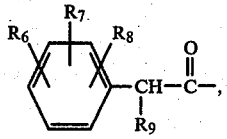

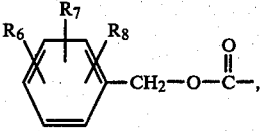

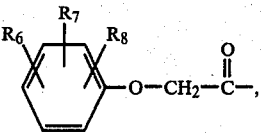

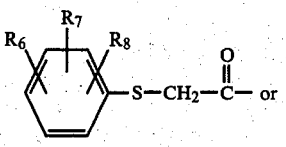

-continued

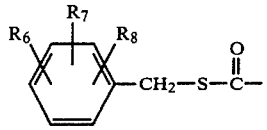

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_9$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

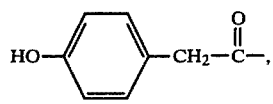

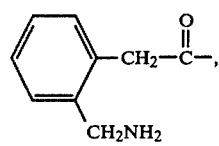

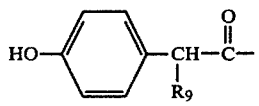

($R_9$ is preferably a carboxyl salt or sulfo salt) and

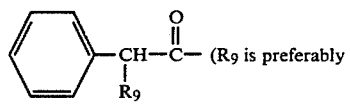 ($R_9$ is preferably a carboxyl salt or sulfo salt).

(c) Heteroaromatic groups having the formula

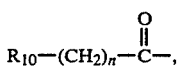

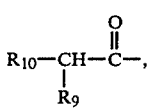

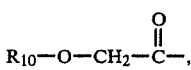

$$R_{10}-S-CH_2-\overset{O}{\underset{\|}{C}}-, \text{ or}$$

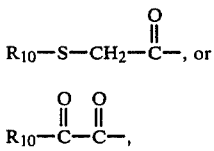

wherein n is 0, 1, 2 or 3; $R_9$ is as defined above; and $R_{10}$ is a substituted or unsubstituted 5-,6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazinyl, thiazolyl, morpholinyl, pyrimidinyl and tetrazolyl. Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R_{10}$ is 2-amino-4-thiazolyl, 2-amino-5-halo-4-thiazolyl, 4-aminopyrimidin-2-yl, 5-amino-1,2,4-thiadiazol-5-yl, 2-thienyl or 2-furanyl.

(d) [[(4-Substituted-2,3-dioxo-1-piperazinyl)carbonyl]amino]arylacetyl groups having the formula

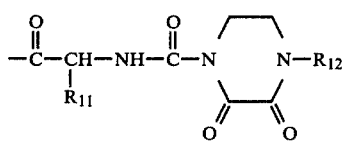

wherein $R_{11}$ is an aromatic group (including carbocyclic aromatics such as those of the formula

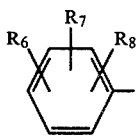

and heteroaromatics as included within the definition of $R_{10}$); and $R_{12}$ is alkyl, substituted alkyl (wherein the alkyl group is substituted with one or more halogen, cyano, nitro, amino or mercapto groups), arylmethyleneamino (i.e., $-N=CH-R_{11}$ wherein $R_{11}$ is as defined above), arylcarbonylamino (i.e.,

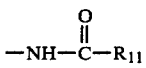

wherein $R_{11}$ is as defined above) or alkylcarbonylamino.

Preferred [[(4-substituted-2,3-dioxo-1-piperazinyl)carbonyl]amino]arylacetyl groups include those wherein $R_{12}$ is ethyl phenylmethyleneamino or 2-furylmethyleneamino.

(e) (Substituted oxyimino)arylacetyl groups having the formula

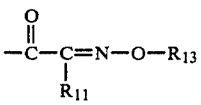

wherein $R_{11}$ is as defined above and $R_{13}$ is hydrogen, alkyl, cycloalkyl, alkylaminocarbonyl, arylaminocarbonyl (i.e.,

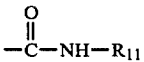

wherein $R_{11}$ is as defined above) or substituted alkyl (wherein the alkyl group is substituted with 1 or more halogen, cyano, nitro, amino, mercapto, alkylthio, aromatic group (as defined by $R_{11}$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy (phenylmethoxy)phosphinyl, or dialkoxyphosphinyl substituents).

Preferred (substituted oxyimino)arylacetyl groups include those wherein $R_{11}$ is 2-amino-4-thiazolyl. Also preferred are those groups wherein $R_{13}$ is methyl, ethyl, carboxymethyl, or 2-carboxyisopropyl.

(f) (Acylamino)arylacetyl groups having the formula

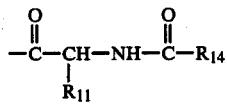

wherein $R_{11}$ is as defined above and $R_{14}$ is

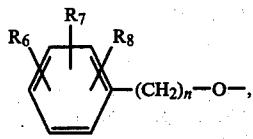

amino, alkylamino, (cyanoalkyl)amino, amido, alkylamido, (cyanoalkyl)amido,

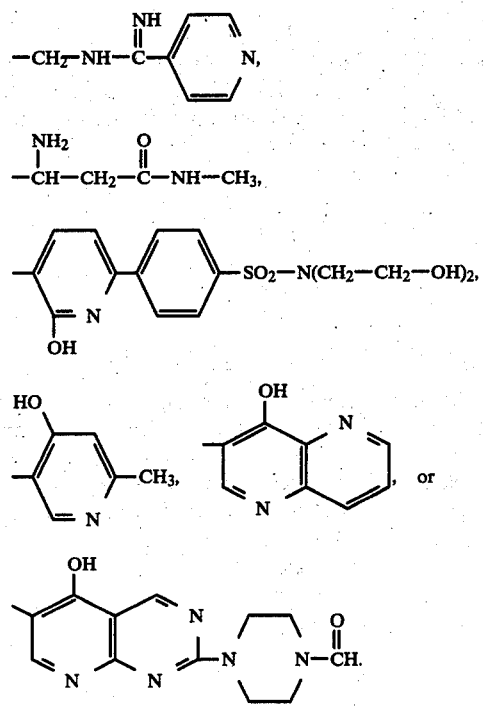

Preferred (acylamino)arylacetyl groups of the above formula include those groups wherein $R_{14}$ is amino, or amido. Also preferred are those wherein $R_{11}$ is phenyl or 2-thienyl.

(g) [[[3-Substituted-2-oxo-1-imidazolidinyl]carbonyl]amino]arylacetyl groups having the formula

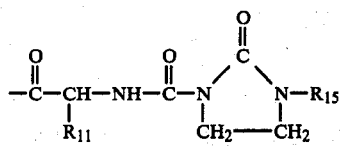

wherein $R_{11}$ is as defined above and $R_{15}$ is hydrogen, alkylsulfonyl, arylmethyleneamino (i.e., —N=CH—$R_{11}$ wherein $R_{11}$ is as defined above),

(wherein $R_{16}$ is hydrogen, alkyl or halogen substituted alkyl), aromatic group (as defined by $R_{11}$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_{11}$ is phenyl or 2-thienyl. Also preferred are those groups wherein $R_{15}$ is hydrogen, methylsulfonyl, phenylmethyleneamino or 2-furylmethyleneamino.

The term "cation", as used throughout the specification, refers to any positively charged atom or group of atoms. The "—O—SO$_3^\ominus$M$^\oplus$" substituent on the nitrogen atom of the β-lactams of this invention encompasses all sulfate salts. Pharmaceutically acceptable salts are, of course, preferred, although other salts are also useful in purifying the products of this invention or as intermediates for the preparation of pharmaceutically acceptable salts. The cationic portion of the sulfonic acid salts of this invention can be obtained from either organic or inorganic bases. Such cationic portion includes, but is not limited to, the following ions: ammonium; substituted ammonium, such as alkylammonium (e.g., tetra-n-butylammonium, referred to hereinafter as tetrabutylammonium); alkali metal, such as lithium, sodium and potassium; alkaline earth metal, such as calcium and magnesium; pyridinium; dicyclohexylammonium; hydrabaminium; benzathinium; N-methyl-D-glucaminium.

As set forth in formula I, and in the definitions following formula I, M$^\oplus$ can be hydrogen provided the $R_1$ group contains a basic function. Such compounds are often referred to in the art as "inner salts" by virtue of a positive and negative charge in the molecule.

Some of the compounds of this invention may be crystallized or recrystallized from solvents containing water. In these cases water of hydration may be formed. This invention contemplates stoichiometric hydrates as well as compounds containing variable amounts of water that may be produced by processes such as lyophilization.

β-Lactams having a sulfate substituent in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nuclues is the same as the configuration at the carbon atom in the 6-position of naturally occurring penicillins (e.g., penicillin G) and as the configuration at the carbon atom in the 7-position of naturally occurring cephamycins (e.g., cephamycin C).

With respect to the preferred β-lactams of formulas I and Ia, the structural formulas have been drawn to show the stereochemistry at the chiral center in the 3-position. Because of the nomenclature convention, those compounds of formulas I and Ia wherein $R_2$ is hydrogen have the S-configuration and those compounds of formulas I and Ia wherein $R_2$ is alkoxy have the R configuration.

Also included within the scope of this invention are racemic mixtures which contain the above-described β-lactams.

DETAILED DESCRIPTION OF THE INVENTION

β-Lactams having a sulfate (—O—SO$_3^\ominus$M$^\oplus$) substituent in the 1-position and an acylamino substituent in the 3-position have activity against a range of gram-negative and gram-positive organisms. The sulfate substituent is essential to the activity of the compounds of this invention.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The β-lactams of this invention can be prepared from the corresponding hydroxamic acid having the formula

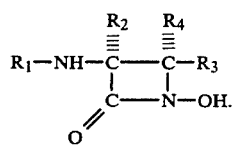

II

A compound of formula II can be O-sulfated by reacting the precursor compound with a complex of pyridine and sulfur trioxide. The reaction can be run in an organic solvent, preferably pyridine. This reaction yields a compound of formula I wherein M$^\oplus$ is pyridinium ion. Instead of using a pre-formed complex of pyridine and sulfur trioxide, the complex can be formed in situ, e.g., using chlorosulfonyltrimethylsilyl ester and pyridine as reagents. Alternatively, a complex of dimethylformamide sulfur trioxide or 2,6-lutidine-sulfurtrioxide can be used.

Using conventional techniques (e.g., ion-exchange resins, crystallization, or ion-pair extraction) the pyridinium salt formed by the above procedure can be converted to other salts. These techniques are also useful for converting the products of formula I or any of the intermediates described herein to other salts.

Compounds of formula II can be prepared from an amino acid having the formula

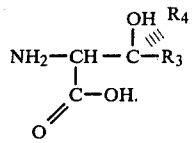

III

The amino group is first protected with a classical protecting group (e.g., t-butoxycarbonyl, benzyloxycarbonyl, o-nitrophenylsulfenyl, etc.), yielding a compound having the formula

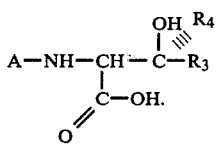

IV

In formula IV, and throughout the specification, the symbol "A" refers to a nitrogen protecting group.

The carboxyl group of a protected amino acid of formula IV is then reacted with an amine salt having the formula $$Y\text{-}O\text{-}NH_3^\oplus Cl^\ominus,$$

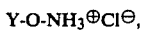

In formula V, and throughout the specification, the symbol "Y" refers to benzyl or pivaloyl. The reaction proceeds in the presence of a coupling agent such as 1-ethyl-3-(3-dimethylaminopropyl) carbodiimide or dicyclohexylcarbodiimide, and yields a compound having the formula

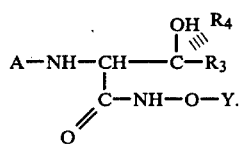

VI

The hydroxyl group of a compound of formula VI is converted to a leaving group, using, for example, a classical reagent such as methanesulfonyl chloride (methanesulfonyl is referred to hereinafter as "Ms").

The fully protected compound having the formula

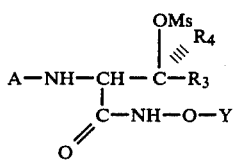

VII is cyclized by treatment with base, e.g., potassium carbonate. The reaction is preferably carried out in an organic solvent such as acetone, under reflux conditions, and yields a compound having the formula

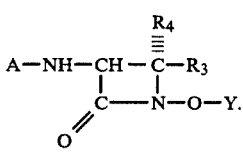

VIII

Alternatively, cyclization of a compound of formula VI can be accomplished without first converting the hydroxyl group to a leaving group. Treatment of a compound of formula VI with triphenylphosphine and diethylazodicarboxylate, yields a compound of formula VIII.

Both of the methods disclosed above for ring closure of a compound of formula VI result in the inversion of the stereochemistry of the R₃ and R₄ substituents.

Deprotection of the 3-amino substituent of a compound of formula VIII can be accomplished using art-recognized techniques. If, for example, the protecting group is t-butoxycarbonyl, trifluoroacetic acid can be used to deprotect the amino group. If the protecting group is benzyloxycarbonyl catalytic (e.g., palladium on charcoal) hydrogenation can be used. If the protecting group is o-nitrophenylsulfenyl, p-toluenesulfonic acid can be used in combination with p-thiocresol. The deprotected compound has the formula

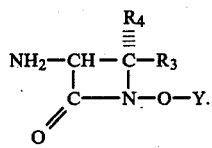

Well known acylation techniques can be used to convert a compound having the formula IX to a compound having the formula

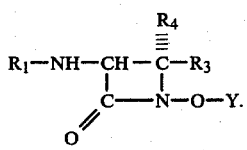

Exemplary techniques include reaction with a carboxylic acid (R₁-OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group (R₁) contains reactive functionality (such as amino or carboxyl groups) it may be necessary to first protect these functional groups, then carry out the acylation reaction, and finally deprotect the resulting product.

Conversion of a compound of formula X to the corresponding compound having a 3-alkoxy substituent can be accomplished by first halogenating the amide nitrogen to obtain a compound having the formula

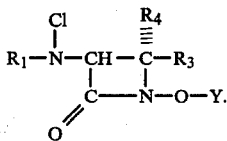

Reagents and procedures for N-chlorinating amides are known in the art. Exemplary reagents are tert.-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of a compound of formula XI with an alkoxylating agent, e.g., an alkali metal alkoxide, yields a compound (in combination with its enantiomer) having the formula

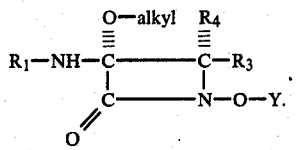

The reaction can be run in an organic solvent, e.g., a polar organic solvent such as tetrahydrofuran, at a reduced temperature.

Alternatively, a compound of formula X can be converted to a compound of formula XII using a single step procedure. The alkoxylating agent can first be mixed with a compound of formula X and the N-chlorinating reagent then added to the reaction mixture.

Reduction of a compound of formula X or XII to yield the corresponding compound of formula II, i.e.,

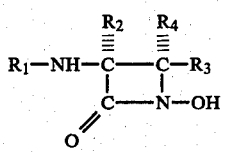

can be accomplished by catalytic hydrogenation or, if Y is pivaloyl, by treatment with a base such as sodium sulfide or sodium hydroxide.

Alternatively, α-benzyloxycarbonyl-β-aminoxy-D-alanine, methyl ester hydrochloride, or other compounds having the "NH—O—" grouping, can be used in place of an amine salt of formula V in the above described synthesis.

An alternative synthesis for the compounds of this invention wherein R₂ is hydrogen comprises preparation of a compound of formula VIII followed by deprotection of the 1-hydroxy group of that compound to yield a compound having the formula

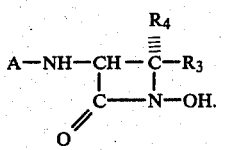

Deprotection can be accomplished using art-recognized procedures, e.g., if Y is pivaloyl, treatment with hydrogen peroxide and a base or treatment with sodium sulfide, or if Y is benzyl, by hydrogenolysis.

Sulfation of a compound of formula VIIIa using the above-described procedures (i.e., reaction of the precursor compound with a complex of pyridine and sulfur trioxide, dimethylformamide and sulfur trioxide or 2,6-lutidine and sulfur trioxide) yields a compound having the formula

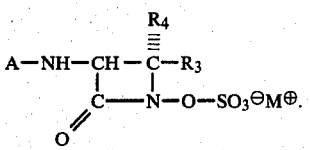

Removal of the protecting group "A" from a compound of formula XIII yields a key intermediate having the formula

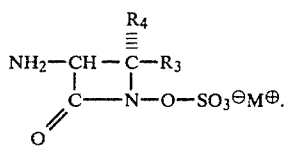   XIV

The technique used for removal of the protecting group will depend on the particular protecting group. For example, if A is benzyloxycarbonyl, catalytic hydrogenation can be used.

Acylation of an intermediate of formula XIV using any of the techniques described above yields a corresponding product of formula V wherein $R_2$ is hydrogen.

The following examples are specific embodiments of this invention.

EXAMPLE 1

(3S-trans)-4-Methyl-2-oxo-3-[(phenylacetyl)amino]-1-azetidinyl sulfate, pyridine salt

(A) N-(Phenylacetyl)-L-threonine

L-Threonine (35.7 g) is dissolved in 1 N sodium hydroxide (1 liter) and chilled to $-5°$ to $-10°$ C. To the cold, mechanically stirred solution is added dropwise phenylacetyl chloride (46.3 g). The reaction mixture is stirred for about 16 hours as the temperature rises to 26° C. The mixture is washed with ether, acidified to pH 2 with hydrochloric acid, and extracted with ethyl acetate (two times). The combined extracts are dried over sodium sulfate and concentrated under reduced pressure until crystalline solids form. Ether is added to the mixture and the crystals are collected (34.8 g); melting point 161°–163° C.

(B) $N^2$-(Phenylacetyl)-N-(phenylmethoxy)-L-threoninamide

N-(Phenylacetyl)-L-threonine (9.5 g) is suspended in water (approximately 50 ml), and a solution of O-benzylhydroxylamine hydrochloride (7.04 g) in water (50 ml) is added. The pH of the stirred mixture is adjusted to 4.2 with 1 N potassium hydroxide, and a solution of 8.43 g of 1-ethyl-3-(3-dimethylaminopropyl)carbodiimide hydrochloride in water (50 ml) is added. The pH is maintained at 4.2 with 1 N hydrochloric acid. After thirty minutes an oily precipitate is present in the reaction vessel. The product is partitioned between ethyl acetate and brine, and the organic layer is then dried over sodium sulfate and concentrated to a solid (8.7 g).

(C) (3S-trans)-4-Methyl-3-(phenylacetyl)-1-(phenylmethoxy)-2-azetidinone

To a cold (0° C.) solution of $N^2$-(phenylacetyl)-N-(phenylmethoxy)-L-threoninamide (7.5 g) in dry tetrahydrofuran (200 ml) is added diethylazodicarboxylate (4.2 g) followed by triphenylphosphine (6.34 g). The reaction mixture is stirred for about 16 hours at 26° C. under nitrogen. The solvent is then removed, and the residue chromatographed on silica gel (ether/hexane) to afford the title compound (2.0 g) white solids. Recrystallization from chloroform/hexane affords a purified sample, melting point 97°–99° C.

(D) (3S-trans)-1-Hydroxy-4-methyl-3-[(phenylacetyl)amino]-2-azetidinone

A solution of (3S-trans)-4-methyl-3-(phenylacetyl)-1-(phenylmethoxy)-2-azetidinone (0.5 g) in ethanol (15 ml) containing 0.250 of 10% palladium on charcoal is hydrogenated at 26° C. for one hour. The reaction mixture is filtered, the catalyst washed with ethanol, and the combined filtrates evaporated to an oily residue. Ether (approximately 10 ml) is added and the resulting solids are hardened and collected yielding 0.34 g of the title compound, melting point 118°–135° C., dec.

Anal. Calc'd. for $C_{12}H_{14}N_2O_3$: C, 61.52; H, 6.02; N, 11.96. Found: C, 61.06; H, 6.03; N, 11.80.

(E) (3S-trans)-4-Methyl-2-oxo-3-[(phenylacetyl)-amino]-1-acetidinyl sulfate, pyridine salt To a solution of (3S-trans)-1-hydroxy-4-methyl-3-[(phenylacetyl)amino]-2-azetidinone (0.225 g) in dry pyridine (9 ml) is added molecular sieves 4 A (1 ml) followed by pyridinesulfur trioxide complex (0.61 g). The reaction mixture is stirred under nitrogen for five hours at 26° C., filtered and concentrated under reduced pressure. Purification on HP-20 resin (water/acetone) affords 0.13 g of the product as a hygroscopic solid.

Anal. Calc'd. for $C_{17}H_{19}N_3O_6S.H_2O$: C, 49.62; H, 5.14; N, 10.21; S, 7.79. Found: C, 50.37; H, 5.07; N, 10.32; S, 7.73.

EXAMPLE 2

[3S-[3α(R*),4β]]-3-[[[[(4-Ethyl-2,3-dioxo-1-piperazinyl)carbonyl]amino]phenylacetyl]amino]-4-methyl-2-oxo-1-azetidinyl sulfate, pyridine salt (1:1)

(A) 2-Nitrophenylthio-L-threonine

L-threonine (11.9 g) is added to dioxane (125 ml) and 2 N sodium hydroxide (50 ml). To the vigorously stirred solution, o-nitrophenylsulfenyl chloride (20.9 g) is added in ten equal portions over fifteen minutes, while 2 N sodium hydroxide (60 ml) is slowly added dropwise. After five more minutes the reaction mixture is diluted with water (400 ml) and acidified to pH 2.5 with 10% potassium bisulfate. The organic layer is immediately extracted with ethyl acetate (three 200 ml portions), and the combined extracts are dried over sodium sulfate, and then concentrated to an oil. The product crystallizes on scratching (20.0 g). Recrystallization of 17 g from acetone/hexane affords 9.5 g of crystals, melting point 145°–148° C. which are stored in a freezer and used promptly.

(B) $N^2$-[(2-Nitrophenyl)thio]-N-(phenylmethoxy)-L-threoninamide

2-Nitrophenylthio-L-threonine (39.0 g) and O-benzylhydroxylamine hydrochloride (22.92 g) are suspended in water (500 ml) and with vigorous stirring the pH is adjusted to 4.2 with 1 N sodium hydroxide. A solution of 1-ethyl-3-(3-dimethylaminopropyl)carbodiimide hydrochloride in water (100 ml) is added portionwise, while the pH is controlled at 4.2 with addition of 10% potassium bisulfate. The addition lasts five minutes, and stirring and pH control is continued for an additional thirty minutes, whereupon a heavy granular precipitate is present. The reaction mixture is extracted with ethyl acetate (four 300 ml portions) and the combined extracts are dried over sodium sulfate and concentrated to an oil (approximately 50 g).

Chromatography on SilicAR CC-7 (2 kg, methylene chloride→50% methylene chloride/ethylacetate) affords the produce as a foam (19.5 g). A portion is crystallized and recrystallized from acetone/hexane to provide an analytical sample, melting point 130°-133° C.

(C)
(3S-trans)-4-Methyl-3-[[(2-nitrophenyl)thio]amino]-1-(phenylmethoxy)-2-azetidinone To a cold solution (0° C.) of $N^2$-[(2-nitrophenyl)thio]-N-(phenylmethoxy)-L-threoninamide (9.4 g) in pyridine (34 ml) is added methanesulfonyl chloride (8.58 g). After two hours at 0° C. the mixture is poured into ice water (100 ml) and extracted with ethyl acetate (five 100 ml portions). The extracts are washed with ice-cold 10% potassium bisulfate (four 100 ml portions), dried over sodium sulfate, and concentrated under reduced pressure without heat, yielding 9.6 g of a residue.

A solution of the residue in acetone (125 ml), is added dropwise over thirty-five minutes to a refluxing mixture of anhydrous potassium carbonate (10 g) and acetone (approximately 600 ml). After 2.5 hours the mixture is cooled to 26° C. filtered, and evaporated to a foam. Chromatography on SilicAR CC-7 (methylene chloride/hexane 9:1→methylene chloride) affords the product as a clear oil (2.15 g). Crystallization and recrystallization from chloroform/hexane produces an analytical sample, melting point 97°-100° C.

(D)
(3S-trans)-3-Amino-4-methyl-1-(phenylmethoxy)-2-azetidinone, toluenesulfonate To a stirred solution of (3S-trans)-4-methyl-3-[[(2-nitrophenyl)thio]amino]-1-phenylmethoxy)-2-azetidinone (1.07 g) in methylene chloride (20 ml) is added p-toluenesulfonic acid (0.57 g) and p-thiocresol (0.74 g). The reaction mixture is stirred under nitrogen for two hours, whereupon the solvents are removed in vacuo, and the residue is triturated with ether (four 25 ml portions), to afford 0.9 g of the title compound.

(E)
(3S-trans)-3-[[[[(4-Ethyl-2,3-dioxo-1-piperazinyl)carbonyl]amino]phenylacetyl]amino]-4-methyl-1-(phenylmethoxy)-2-azetidinone A suspension of α-[[(4-ethyl-2,3-dioxo-1-piperazinyl)-carbonyl]amino]benzeneacetic acid (0.879 g) hydroxybenzotriazole (0.42 g), and dicyclohexylcarbodiimide (0.56 g), in dimethylformamide (15 ml) is stirred at 26° C. for one hour, at which point a solution of (3S-trans)-3-amino-4-methyl-1-(phenylmethoxy)-2-azetidinone, toluenesulfonate (0.95 g) and diisopropylethylamine (0.44 ml) in dimethylformamide (5 ml) is added. The reaction mixture is stirred at room temperature for about 16 hours, then poured into water (100 ml) and extracted with ethyl acetate (three 100 ml portions). The combined organic extracts are washed with water (three 100 ml portions) and aqueous sodium bicarbonate solution (one 100 ml portion), then dried over sodium sulfate and concentrated under reduced pressure to a semi-solid residue. Liquid chromatography (ethyl acetate) affords the desired product as a foam (0.599 g). Recrystallization from chloroform/isopropyl ether yields the title compound, melting point 100°-105° C.

(F)
(3S-trans)-3-[[[[(4-Ethyl-2,3-dioxo-1-piperazinyl)carbonyl]amino]phenylacetyl]amino]-1-hydroxy-4-methyl-2-azetidinone (3S-trans)-3-[[[[(4-ethyl-2,3-dioxo-1-piperazinyl)carbonyl]amino]phenylacetyl]amino]-4-methyl-1-(phenylmethoxy)-2-azetidinone (0.270 g) is dissolved in ethanol (25 ml) and hydrogenated over 10% palladium on charcoal catalyst (130 mg) for two hours. The reaction mixture is filtered and concentrated to a solid (0.220 g).

(G)
[3S-[3α(R*),4β]]-3-[[[[(4-Ethyl-2,3-dioxo-1-piperazinyl)carbonyl]amino]phenylacetyl]amino]-4-methyl-2-oxo-1-azetidinyl sulfate, pyridine salt (1:1)

To a solution of (3S-trans)-3-[[[[(4-ethyl-2,3-dioxo-1-piperazinyl)carbonyl]amino]phenylacetyl]amino]-1-hydroxy-4-methyl-2-azetidinone (0.220 g) in pyridine (7 ml) is added 4 A molecular sieves (approximately 1 ml) and pyridine-sulfur trioxide complex (0.33 g). After stirring under nitrogen at 26° C. for 4.5 hours, the reaction mixture is filtered and concentrated to an oil. Chromatography on HP 20 AG resin (water/acetone) followed by lyophilization of the appropriate fractions affords the desired product as a powder (0.080 g).

Anal. Calc'd. for $C_{19}H_{23}N_5O_9S.C_5H_5N.2H_2O$: C, 47.05; H, 5.26; N, 13.72. Found: C, 46.36; H, 4.74; N, 13.42.

EXAMPLE 3
[3S(Z)]-3-[[(2-Amino-4-thiazolyl)(methoxyimino)acetyl]amino]-2-oxo-1-azetidinyl sulfate, potassium salt (A) α-[(Phenylmethyl)oxy]-β-aminoxy-D-alanine methyl ester hydrochloride Hydrogen chloride gas is bubbled into ice cold methanol (200 ml) for twenty minutes. α-[(Phenylmethyl)oxy]-D-cycloserine (5.0 g) is added, and the cloudy solution is stirred at 26° C. for twelve hours. The reaction mixture is filtered and concentrated into a semisolid residue which upon titration with ether (two 200 ml portions) gives 4.6 g of solid, melting point 110°-112° C.

[A more quantitative alternative procedure comprises preparation of ca. 1 N methanolic hydrogen chloride solution by adding 7.1 ml acetyl chloride dropwise to 100 ml of chilled, stirred, methanol. After thirty minutes, α-[(phenylmethyl)oxy]cycloserine (5.0 g) is added, the mixture is evaporated after 12 hours, and the residue is triturated with ether. The resulting crystalline mass is collected by filtration and dried in vacuo yielding 5.7 g of the title compound.]

(B)
$N^2$-[[(Phenylmethyl)oxy]carbonyl]-N-[2-[[[(phenylmethyl)oxy]carbonyl]amino]-3-methoxy-3-oxopropoxy]-L-serinamide To a suspension of N-[[(phenylmethoxy]oxy]carbonyl]-L-Serine (3.46 g) in water (15 ml), is added an aqueous (15 ml) solution of α-[(phenylmethyl)oxy]-β-aminoxy-D-alanine methyl ester hydrochloride (4.49 g). The mixture is vigorously stirred (air stirrer), while adjusting to pH 4.2 with 1 N potassium hydroxide. A solution of 1-ethyl-3-(3-dimethylaminopropyl)carbodiimide in water (10 ml) is added portionwise over five minutes, while the pH is maintained at 4.2 by addition of 1 N hydrochloric acid. After stirring for an additional twenty minutes, the reaction mixture is saturated with sodium chloride and extracted with ethyl acetate (five times). The combined ethyl acetate extracts are dried over sodium sulfate and concentrated under reduced pressure to a viscous oil (5.8 g).

(C)
(3S)-1-Hydroxy-3-[[[(phenylmethyl)oxy]carbonyl]amino]-2-azetidinone

To a cold (0°–5° C.) solution of $N^2$-[[[(phenylmethyl)oxy]carbonyl]-N-[2-[[[(phenylmethyl)oxy]carbonyl]amino]-3-methoxy-3-oxopropoxy]-L-serinamide (6.08 g) in distilled tetrahydrofuran (100 ml) is added triphenylphosphine (3.6 g) followed by diethylazodicarboxylate (2.15 ml, 2.38 g). The reaction mixture is allowed to stir for twelve hours under nitrogen, whereupon 7.0 ml of 1,8-diazabicyclo[5.4.0.]undecan-7-ene is added. After 30 minutes, tetrahydrofuran is removed by evaporation and the resulting residue is partitioned between ethyl acetate and saturated sodium bicarbonate. The aqueous layer is washed once with ethyl acetate, then adjusted to pH 2 with saturated potassium bisulfate, and extracted with ethyl acetate (five times). The combined extracts are dried and concentrated to a crystalline solid (1.8 g). A portion is recrystallized from acetone/hexane (two times) to give an analytical sample, melting point 128°–131° C.

(D)
(3S)-3-[[[(Phenylmethyl)oxy]carbonyl]amino]-2-oxo-1-azetidinyl sulfate, tetrabutylammonium salt To a solution of (3S)-1-hydroxy-3-[[[(phenylmethyl)oxy]carbonyl]amino]-2-azetidinone (1.1 g) in dry pyridine (45 ml) containing 4 A molecular sieves (ca. 1 ml) is added pyridine-sulfur trioxide complex (1.48 g). After stirring for two hours at 26° C., under nitrogen, the pyridine is removed under reduced pressure, and the residue is partitioned between pH 4.3 buffer (0.5 M monobasic potassium phosphate, 50 ml) and ethyl acetate (50 ml). The aqueous layer is washed once more with ethyl acetate (50 ml), then treated with tetrabutyl ammonium hydrogen sulfate (1.57 g), and extracted with methylene chloride (three 50 ml portions). The combined organic extracts are dried over sodium sulfate and concentrated to a viscous oil (1.81 g). The material is purified on SilicAR CC-4 using methylene chloride/methanol (1% to 8%) as eluant to afford 0.71 g of oil.

(E)
[3S(Z)]-3-[[(2-Amino-4-thiazolyl)(methoxyimino)acetyl]amino]-2-oxo-1-azetidinyl sulfate, potassium salt A solution of (3S)-3-[[[(phenylmethyl)oxy]carbonyl]amino]-2-oxo-1-azetidinyl sulfate, tetrabutylammonium salt (0.70 g) in dimethylformamide is hydrogenated for 6.5 hours using 10% palladium on charcoal catalyst (0.35 g). After filtration to remove catalyst, (Z)-2-amino-α-(methoxyimino)-4-thiazoleacetic acid (0.251 g) dicyclohexylcarbodiimide, followed by hydroxybenzotriazole (0.191 g) are added to the mixture and it was stirred for about 16 hours at 26° C. The reaction mixture is concentrated under high vacuum (40° C.), diluted with acetone (25 ml), and then filtered. The solids are washed with a small amount of acetone and the combined filtrate is treated with a solution of potassium perfluorobutane sulfonate (0.425 g) in acetone (2 ml). Precipitation occurs at once. Ether (20 ml) is added and the precipitated solids are collected by filtration (0.250 g). Purification by HP-20AG chromatography using water-acetone (0–5%) as eluant gives the product as a powder after lyophilization (0.045 g).

Anal. Calc'd. for $C_9H_{10}N_5S_2O_7K$: C, 26.79; H, 2.50; N, 17.36; S, 15.89; K, 9.69. Found: C, 29.63; H, 3.16; N, 16.95; S, 17.69; K, 1.78.

The product is a mixture of the potassium salt and zwitterion, and displays appropriate IR and NMR spectra.

EXAMPLE 4
(S)-2-Oxo-3-[(phenylacetyl)amino]-1-azetidinyl sulfate, pyridine salt (A)
$N^2$-(Phenylacetyl)-N-[(phenylmethyl)oxy]-L-serinamide N-Phenylacetyl-L-serine (8.8 g), 1-hydroxybenzotriazole hydrate (6.03 g) and o-benzylhydroxylamine (4.84 g) are dissolved in tetrahydrofuran (450 ml) and chilled to 0° C. A solution of dicyclohexylcarbodiimide (8.1 g), in tetrahydrofuran (50 ml) is added over a 0.5 hour period. The reaction is allowed to warm to 26° C. and stir for about 16 hours. The mixture is filtered, and the filtrate concentrated under reduced pressure to a semi-solid residue. The addition of ethyl acetate (50 ml) causes crystallization. The solids are collected and dried (6.9 g, melting point 150°–151° C.).

The filtrate is washed with sodium bicarbonate, water, potassium bisulfate, and water (twice), and then dried over sodium sulfate and concentrated until a second crop of crystals is obtained (2.6 g), melting point 131°–135° C.

(B)
(S)-3-[(Phenylacetyl)amino]-1-[(phenylmethyl)oxy]-2-azetidinone

To a cold solution (0° C.) of $N^2$-(phenylacetyl)-N-[(phenylmethyl)oxy]-L-serinamide (6.88 g) in distilled tetrahydrofuran (300 ml), under nitrogen, is added triphenylphosphine (11.20 g) followed by diethylazodicarboxylate (6.60 ml). The solution is allowed to warm to 26° C. and stirred for twelve hours. After removal of solvent under reduced pressure the resulting residue is applied to a silica gel column (eluant ether/hexane→ether). Combination of fractions gives two batches; 1.0 g (pure) and 2.5 g (ca. 60% pure) (total yield ca. 2.2 g). The pure material is recrystallized from ethyl acetate/hexane to give solids; melting point 130°–131° C.

(C)
(S)-1-Hydroxy-3-[(phenylacetyl)amino]-2-azetidinone

To an ethanolic (100 ml) solution of (S)-3-[(phenylacetyl)amino]-1-[(phenylmethyl)oxy]-2-azetidinone (0.8 g, contaminated with triphenylphosphine) is added 10% palladium on charcoal catalyst (0.4 g) and the mixture is hydrogenated under ca. 1 atom pressure for one hour. The reaction mixture is filtered through prewashed Celite and concentrated under reduced pressure to an oily residue. The product is partitioned between 50% sodium bicarbonate solution and ethyl acetate. The aqueous layer is acidified with potassium bisulfate and extracted with ethyl acetate (three 50 ml portions). The combined extracts are dried over sodium sulfate and concentrated to a crystalline solid (ca. 200 mg). Recrystallization from methanol/chloroform affords an analytical sample, melting point 145°–146° C. dec.

(D) (S)-2-Oxo-3-[(phenylacetyl)amino]-1-azetidinyl sulfate, pyridine salt (S)-1-Hydroxy-3-[(phenylacetyl)amino]-2-azetidinone (0.150 g) is dissolved in dry pyridine (10 ml) containing 4A molecular sieves. Pyridinesulfur trioxide complex (0.216 g) is added and the solution is stirred under nitrogen for two hours. After concentration under reduced pressure, and vacuum drying, the product is purified on HP-20AG (25 ml). Elution with water and then 5% acetone/water, followed by lyophilization of the desired fractions affords the product (0.110 g) as a hygroscopic powder; $[\alpha]_D^{26} = +5.9$ (c=0.645, water).

Anal. Calc'd. for $C_{16}H_{17}N_3O_6S \cdot 0.5\ H_2O$: C, 49.15; H, 4.74; N, 10.71; S, 8.34. Found: C, 49.47; H, 4.67; N, 10.81; S, 8.25.

EXAMPLE 5

(S)-2-Oxo-3-[(phenylacetyl)amino]-1-azetidinyl sulfate, potassium salt (S)-2-Oxo-3-[(phenylacetyl)amino]-1-azetidinyl sulfate, pyridine salt (1.5 g; see example 4) is dissolved in water and applied to a column containing 150 ml Dowex 50-X2K resin. Elution with 1500 ml double distilled water gives five 300 ml fractions which are lyophilized. Fraction 1 contains 1.33 g of the title compound.

Anal. Calc'd. for $C_{11}H_{11}N_2O_6S \cdot K \cdot 1.5\ H_2O$: C, 36.15; H, 3.86; N, 7.66; S, 8.77; K, 10.70 Found: C, 36.14; H, 3.15; N, 7.20; S, 9.81; K, 14.01

EXAMPLE 6

(S)-2-Oxo-3-[(phenylacetyl)amino]-1-azetidinyl sulfate, tetrabutylammonium salt (S)-2-Oxo-3-[(phenylacetyl)amino]-1-azetidinyl sulfate, potassium salt (93 mg, see example 5) is dissolved in water (5 ml) and tetrabutylammonium hydrogen sulfate (102 mg) is added. The solution is shaken for a few minutes, saturated with sodium chloride and extracted with methylene chloride (four times). The combined extracts are dried over sodium sulfate and concentrated under reduced pressure to an oil (112 mg).

Anal. Calc'd. for $C_{11}H_{11}N_2O_6S \cdot C_{16}H_{36}N$: C, 59.85; H, 8.74; N, 7.75; S, 5.91. Found: C, 60.25; H, 9.40; N, 7.13; S, 5.51.

EXAMPLE 7

(S)-2-Oxo-3-[(2-thienylacetyl)amino]-1-azetidinyl sulfate, potassium salt

A solution of (3S)-3-[[[(phenylmethyl)oxy]carbonyl]amino]-2-oxo-1-azetidinyl sulfate, tetrabutylammonium salt (1.0 g; see example 3D) in dimethylformamide (20 ml) containing 10% palladium on charcoal (0.5 g) is hydrogenated for six hours at 26° C. The mixture is filtered to remove catalyst. Hydroxybenzotriazole (0.261 g) is added, followed by thiopheneacetic acid (0.243 g) and finally dicyclohexylcarbodiimide DCC (0.352 g). The reaction mixture is stirred at 26° C. for about 16 hours, and then concentrated at 40° C. under high vacuum. The residue is diluted with acetone (10 ml) and the resulting precipitate is filtered and washed with acetone (2 ml). To the acetone filtrate is added potassium perfluorobutane sulfonate (0.867 g) in acetone (2 ml). The solution is treated with ether (approximately 30 ml) and the precipitate is filtered and dried in high vacuum. Chromatography on HP-20 resin (water→5% acetone/water) affords the product after lyophilization as a solid (51 mg). This material contains approximately 50% potassium perfluorobutane sulfonate.

Anal. Calc'd. for $C_9H_9O_6N_2S_2K$: C, 31.38; H, 2.63; N, 8.14; S, 18.62; K, 11.55. Found: C, 22.58; H, 1.30; N, 4.17; S, 14.63; K, 8.62.

In an attempt to further purify this material, the substance is dissolved in a small amount of acetone and ether is added. The precipitate is collected, dissolved in water and lyophilized. The filtrate is evaporated, dissolved in water and lyophilized. The precipitate gives 13 mg of 60% pure product and the filtrate yields 16 mg of 44% pure product.

EXAMPLE 8

(3S-trans)-3-[(2,6-Dimethoxybenzoyl)amino]-4-methyl-2-oxo-1-azetidinyl sulfate, pyridine (1:1) salt

(A)

(3S-trans)-3-[(2,6-Dimethoxybenzoyl)amino]-4-methyl-1-[(phenylmethoxy)oxy]-2-azetidinone To a cold (−10° C.) solution of (3S-trans)-3-amino-4-methyl-1-(phenylmethoxy)-2-azetidinone, toluenesulfonate (0.95 g; see example 2D) in methylene chloride (50 ml) is added 2,6-dimethoxybenzoyl chloride (0.60 g) and 4-dimethylaminopyridine (0.61 g). The reaction is stirred under nitrogen and allowed to rise to 26° C. over five hours. The reaction mixture is concentrated to an oil and partitioned between ethyl acetate and aqueous hydrogen sulfate solution. The organic layer is washed with aqueous sodium bicarbonate, and brine, dried over sodium sulfate and concentrated to a foam (0.848 g).

(B)

(3S-trans)-3-[(2,6-Dimethoxybenzoyl)amino]-1-hydroxy-4-methyl-2-azetidinone To a stirred solution of (3S-trans)-3-[(2,6-dimethoxybenzoyl)amino]-4-methyl-1-[(phenylmethyl)oxy]-2-azetidinone (0.848 g) in absolute ethanol (20 ml) under nitrogen is added 1,4-cyclohexadiene (8 ml) and freshly prepared palladium black (approximately 0.85 g). After one hour the reaction mixture is filtered and evaporated to a solid (0.605 g).

(C)

(3S-trans)-3-[(2,6-Dimethoxybenzoyl)amino]-4-methyl-2-oxo-1-azetidinyl sulfate, pyridine (1:1) salt To a solution of (3S-trans)-3-[(2,6-dimethoxybenzoyl)amino]-1-hydroxy-4-methyl-2-azetidinone (0.60 g) in dry pyridine (20 ml) under nitrogen is added 4A molecular sieves (approximately 3 ml) and pyridine-sulfur trioxide complex (1.35 g). After three hours the reaction mixture is filtered and the filtrate concentrated and applied to an HP-20AG resin column (acetone/water). The desired fractions are lyophilized to afford the title compound (0.192 g) as a powder.

Anal. Calc'd. for $C_{18}H_{21}N_3SO_8 \cdot 0.5\ H_2O$: C, 48.21; H, 4.94; N, 9.37; S, 7.15. Found: C, 48.23; H, 4.94; N, 9.37; S, 7.10.

EXAMPLES 9–69

Following the procedure of example 3, but substituting the carboxylic acid listed in column I for (Z)-2-amino-α-(methoxyimino)-4-thiazoleacetic acid, yields the potassium salt of the compound listed in column II.

| Column I | Column II |
| --- | --- |
| 9. (Z)-2-amino-α-(ethoxyimino)-4-thiazoleacetic acid | [3S(Z)]-3-[[(2-amino-4-thiazolyl)(ethoxyimino)acetyl]amino]-2-oxo-1-azetidinyl sulfate |
| 10. (E)-2-amino-α-(methoxyimino)-4-thiazoleacetic acid | [3S(E)]-3-[[(2-amino-4-thiazole)(methoxyimino)acetyl]amino]-2-oxo-1-azetidinyl sulfate |
| 11. (Z)-2-amino-α-[(2,2,2-trifluoroethoxy)imino]-4-thiazoleacetic acid | [3S(Z)]-3-[[(2-amino-4-thiazolyl)[(2,2,2-trifluoroethoxy)imino]acetyl]amino]-2-oxo-1-azetidinyl sulfate |
| 12. [(cyanomethyl)thio]acetic acid | (3S)-3-[[[(cyanomethyl)thio]acetyl]amino]-2-oxo-1-azetidinyl sulfate |
| 13. 1H-tetrazole-1-acetic acid | (3S)-3-[(1H-tetrazol-1-ylacetyl)amino]-2-oxo-1-azetidinyl sulfate |
| 14. 2-thiopheneacetic acid | (3S)-3-[(2-thienylacetyl)amino]-2-oxo-1-azetidinyl sulfate |
| 15. (R)-α-[[[(2-oxo-1-imidazolidinyl)carbonyl]amino]benzeneacetic acid | [3S(R*)]-3-[[[[(2-oxo-1-imidazolidinyl)carbonyl]amino]phenylacetyl]amino]-2-oxo-1-azetidinyl sulfate |
| 16. (Z)-α-(methoxyimino)benzeneacetic acid | [3S(Z)]-3-[[(methoxyimino)phenylacetyl[amino[-2-oxo-1-azetidinyl sulfate |
| 17. (Z)-2-amino-α-[[2-(diphenylmethoxy)-1,1-dimethyl-2-oxoethoxy]imino]-4-thiazoleacetic acid | [3S(Z)]-3-[[(2-amino-4-thiazolyl)[[2-(diphenylmethoxy)-1,1-dimethyl-2-oxoethoxy]imino]acetyl]amino]-2-oxo-1-azetidinyl sulfate |
| 18. (Z)-2-amino-α-[[2-(diphenylmethoxy)-2-oxoethoxy]imino]-4-thiazoleacetic acid | [3S(Z)]-3-[[(2-amino-4-thiazolyl)[[2-(diphenylmethoxy)-2-oxoethoxy]imino]acetyl]amino]-2-oxo-1-azetidinyl sulfate |
| 19. (D)-α-[[[(4-methoxyphenyl)methoxy]carbonyl]amino]-2-thiopheneacetic acid | [3S(D)]-3-[[[[[(4-methoxyphenyl)methoxy]carbonyl]amino]-2-thienylacetyl]amino]-2-oxo-1-azetidinyl sulfate |
| 20. (±)-2-amino-α-[[[(4-methoxyphenyl)methoxy]carbonyl]amino]-4-thiazoleacetic acid | [3S(±)]-3-[[(2-amino-4-thiazolyl)[[[(4-methoxyphenyl)methoxy]carbonyl]amino]acetyl]amino]-2-oxo-1-azetidinyl sulfate |
| 21. (±)-α-[[[(4-methoxyphenyl)methoxy]carbonyl]amino]-2-furanacetic acid | [3S(±)]-3-[[2-furanyl[[[(4-methoxyphenyl)methoxy]carbonyl]amino]acetyl]amino]-2-oxo-1-azetidinyl sulfate |
| 22. (L)-α-[[[(4-methoxyphenyl)methoxy]carbonyl]amino]benzeneacetic acid | [3S(L)]-3-[[[[(4-methoxyphenyl)methoxy]carbonyl]amino]phenylacetyl]amino]-2-oxo-1-azetidinyl sulfate |
| 23. (L)-α-[[[(4-methoxyphenyl)methoxy]carbonyl]amino]-2-thiopheneacetic acid | [3S(L)]-3-[[[[[(4-methoxyphenyl)methoxy]carbonyl]amino]-2-thienylacetyl]amino]-2-oxo-1-azetidinyl sulfate |
| 24. (±)-α-[[(methylthio)thioxomethyl]thio]benzeneacetic acid | (3S)-3-[[[[(methylthio)thioxomethyl]thio]phenylacetyl]amino]-2-oxo-1-azetidinyl sulfate |
| 25. (D)-α-[[(4-ethyl-2,3-dioxo-1-piperazinyl)carbonyl]amino]-2-thiopheneacetic acid | [3S(D)]-3-[[[[4-ethyl-2,3-dioxo-1-piperazinyl)carbonyl]amino]-2-thienylacetyl]amino]-2-oxo-1-azetidinyl sulfate |
| 26. (±)-α-[[[(methylamino)carbonyl]amino]-2-thiopheneacetic acid | [3S(±)]-3-[[[[(methylamino)carbonyl]amino]-2-thienylacetyl]amino]-2-oxo-1-azetidinyl sulfate |
| 27. (3S)-α-[(aminooxoacetyl)amino]-2-thiopheneacetic acid | [3S(±)-3-[[[[(aminooxoacetyl)amino]-2-thienyl]acetyl]amino]-2-oxo-1-azetidinyl sulfate |
| 28. (R)-α-[[(4-ethyl-2,3-dioxo-1-piperazinyl)carbonyl]amino]benzeneacetic acid | [3S(R*)]-3-[[[[(4-ethyl-2,3-dioxo-1-piperazinyl)carbonyl]amino]phenylacetyl]amino]-2-oxo-1-azetidinyl sulfate |
| 29. (R)-α-[[[2-oxo-3-[(phenylmethlene)amino]-1-imidazolidinyl]carbonyl]amino]benzeneacetic acid | [3S(R*)]-3-[[[[2-oxo-3-[(phenylmethylene)amino]-1-imidazolidinyl]carbonyl]amino]phenylacetyl]amino]-2-oxo-1-azetidinyl sulfate |
| 30. (R)-α-[[[3-(methylsulfonyl)-2-oxo-1-imidazolidinyl]carbonyl]amino]benzeneacetic acid | [3S(R*)]-3-[[[[3-(methylsulfonyl)-2-oxo-1-imidazolidinyl]carbonyl]amino]phenylacetyl]amino]-2-oxo-1-azetidinyl sulfate |
| 31. (S)-α-hydroxybenzeneacetic acid | [3S(S*)]-3-[(hydroxyphenylacetyl)amino]-2-oxo-1-azetidinyl sulfate |
| 32. (R)-α-hydroxybenzeneacetic acid | [3S(R*)]-3-[(hydroxyphenylacetyl)amino]-2-oxo-1-azetidinyl sulfate |
| 33. (Z)-2-amino-α-[[(diethoxyphosphinyl)methoxy]imino]-4-thiazoleacetic acid | [3S(Z)]-3-[[(2-amino-4-thiazolyl)[[(diethoxyphosphinyl)methoxy]imino]acetyl]amino]-2-oxo-1-azetidinyl sulfate |
| 34. (Z)-2-amino-α-[[2-(1,1-dimethylethoxy)-2-oxo-1-phenylethoxy]imino]-4-thiazoleacetic acid | [3S(Z)]-3-[[(2-amino-4-thiazolyl)[[2-(1,1-dimethylethoxy)-2-oxo-phenylethoxy]imino]acetyl]amino]-2-oxo-1-azetidinyl sulfate |
| 35. (Z)-2-amino-α-[(1H-tetrazol-5-ylmethoxy)imino]-4-thiazoleacetic acid | [3S(Z)]-3-[[(2-amino-4-thiazolyl)[(1H-tetrazol-5-ylmethoxy)imino]acetyl]amino]-2-oxo-1-azetidinyl sulfate |
| 36. (Z)-2-amino-α-[(phenylmethoxy)imino]-4-thiazoleacetic acid | [3S(Z)]-3-[[(2-amino-4-thiazolyl)[(phenylmethoxy)imino]acetyl]amino]-2-oxo-1-azetidinyl sulfate |
| 37. (Z)-2-amino-α-[(2-amino-2-oxoethoxy)imino]-4-thiazoleacetic acid | [3S(Z)]-3-[[[(2-amino-2-oxoethoxy)imino](2-amino-4-thiazolyl)acetyl]amino]-2-oxo-1-azetidinyl sulfate |
| 38. (Z)-2-amino-α-(hydroxyimino)-4-thiazoleacetic acid | [3S(Z)]-3-[[(2-amino-4-thiazolyl)(hydroxyimino)acetyl]amino]-2-oxo-1-azetidinyl sulfate |
| 39. α-sulfophenylacetic acid | (3S)-3-[(phenylsulfoacetyl)amino]-2-oxo-1-azetidinyl sulfate |
| 40. (Z)-2-amino-α-[[2-(1,1-dimethylethoxy)-1-(methylthio)-2-oxoethoxy]imino]-4-thiazoleacetic acid | [3S(Z)]-3-[[(2-amino-4-thiazolyl)[[2-(1,1-dimethylethoxy)-1-(methylthio)-2-oxoethoxy]imino]acetyl]amino]-2-oxo-1-azetidinyl sulfate |
| 41. (Z)-α-(methoxyimino)-2-[[(phenylmethoxy)carbonyl]amino]-4-thiazoleacetic acid | [3S(Z)]-3-[[methoxyimino)[2-[[(phenylmethoxy)carbonyl]amino]-4-thiazolyl]acetyl]amino]-2-oxo-1-azetidinyl sulfate |
| 42. α-azidophenylacetic acid | (3S)-3-[(azidophenylacetyl)amino]-2-oxo-1- |

-continued

| | Column I | Column II |
|---|---|---|
| | | azetidinyl sulfate |
| 43. | (S)-[[[2-oxo-3-(phenylmethylene)amino]-1-imidazolidinyl]carbonyl]amino]-2-thiopheneacetic acid | [3S(S*)]-3-[[[[2-oxo-3-[(phenylmethylene)amino]-1-imidazolidinyl]carbonyl]amino]-2-thienylacetyl]-amino]-2-oxo-1-azetidinyl sulfate |
| 44. | (Z)-2-amino-α-[(1-diphenylmethoxycarbonyl-1-methylethoxy)imino]-4-thiazoleacetic acid | [3S(Z)]-3-[[(2-amino-4-thiazolyl)[(1-diphenylmethoxycarbonyl-1-methylethoxy)imino]acetyl]-amino]-2-oxo-1-azetidinyl sulfate |
| 45. | 2-amino-α-[[2-(1,1-dimethylethoxy)-1-methyl-2-oxoethoxy]imino]-4-thiazoleacetic acid | [3S(Z)]-3-[[[(2-amino-4-thiazolyl)[2-(1,1-dimethylethoxy)-1-methyl-2-oxoethoxy]imino]-acetyl]amino]-2-oxo-1-azetidinyl sulfate |
| 46. | (R)-α-[[(4-ethyl-2,3-dioxo-1-piperazinyl)carbonyl]amino]-4-hydroxybenzeneacetic acid | [3S(R*)]-3-[[[[(4-ethyl-2,3-dioxo-4-piperazinyl)carbonyl]amino](4-hydroxyphenyl)acetyl]-amino]-2-oxo-1-azetidinyl sulfate |
| 47. | (±)-α-[[(4-ethyl-2,3-dioxo-1-piperazinyl)carbonyl]amino]-2-furanacetic acid | [3S(±)]-3-[[[[(4-ethyl-2,3-dioxo-4-piperazinyl)-carbonyl]amino]-2-furanylacetyl]amino]-2-oxo-1-azetidinyl sulfate |
| 48. | (R)-α-[[(4-ethyl-2,3-dioxo-1-piperazinyl)carbonyl]amino]-1,4-cyclohexadieneacetic acid | [3S(R*)]-3-[[1,4-cyclohexadien-1-yl[[(4-ethyl-2,3-dioxo-1-piperazinyl)carbonyl]amino]acetyl]-amino]-2-oxo-1-azetidinyl sulfate |
| 49. | (R)-α-[[[2,3-dioxo-4-[(phenylmethylene)-amino]-1-piperazinyl]carbonyl]amino]-4-hydroxybenzeneacetic acid | [3S(R*)]-3-[[[[2,3-dioxo-4-[(phenylmethylene)-amino]-1-piperazinyl]carbonyl]amino](4-hydroxy-phenyl)acetyl]amino]-2-oxo-1-azetidinyl sulfate |
| 50. | (Z)-2-amino-α-[(1-methylethoxy)imino]-4-thiazoleacetic acid | [3S(Z)]-3-[[(2-amino-4-thiazolyl)[(1-methyl-ethoxy)imino]acetyl]amino]-2-oxo-1-azetidinyl sulfate |
| 51. | (Z)-2-amino-α-(phenoxyimino)-4-thiazoleacetic acid | [3S(Z)]-3-[[(2-amino-4-thiazolyl)(phenoxyimino)-acetyl]amino]-2-oxo-1-azetidinyl sulfate |
| 52. | (R)-α-[[[3-[[(4-hydroxyphenyl)methylene]amino]-2-oxo-1-imidazolidinyl]-carbonyl]amino]benzeneacetic acid | [3S(R*)]-3-[[[[3-[[(4-hydroxyphenyl)methylene]-amino]-2-oxo-1-imidazolidinyl]carbonyl]amino]-phenylacetyl]amino]-2-oxo-1-azetidinyl sulfate |
| 53. | (R)-α-[[[2-oxo-3-[(4-pyridinylmethylene)-amino]-1-imidazolidinyl]carbonyl]amino]-benzeneacetic acid | [3S(R*)]-2-oxo-3-[[[[2-oxo-3-[(4-pyridinyl-methylene)amino]-1-imidazolidinyl]carbonyl]-amino]phenylacetyl]amino]-1-azetidinyl sulfate |
| 54. | (Z)-2-amino-α-[[1-methyl-2-oxo-2-(phenylmethoxy)ethoxy]imino]-4-thiazoleacetic acid | [3S(Z)]-3-[[(2-amino-4-thiazolyl)[[1-methyl-2-oxo-2-(phenylmethoxy)ethoxy]imino]acetyl]amino]-2-oxo-1-azetidinyl sulfate |
| 55. | (Z)-2-amino-α-[(cyclopentyloxy)imino]-4-thiazoleacetic acid | [3S(Z)]-3-[[(2-amino-4-thiazolyl)[(cyclopentyloxy)-imino]acetyl]amino]-2-oxo-1-azetidinyl sulfate |
| 56. | (R)-α-[[1-oxo-2-[[(phenylmethoxy)-carbonyl]amino]ethyl]amino]benzeneacetic acid | [3S(R*)]-2-oxo-3-[[phenyl[[[(phenylmethoxy)-carbonyl]amino]acetyl]amino]acetyl]amino]-1-azetidinyl sulfate |
| 57. | 2-furanacetic acid | (S)-3-[(2-furanylacetyl)amino]-2-oxo-1-azetidinyl sulfate |
| 58. | (R)-α-[[[(2-oxo-3-phenyl-1-imidazolidinyl)carbonyl]amino]benzeneacetic acid | (3S)-2-oxo-3-[[[[(2-oxo-3-phenyl-1-imidazolidinyl)-carbonyl]amino]phenylacetyl]amino]-1-azetidinyl sulfate |
| 59. | (R)-α-[[[2-oxo-3-(phenylmethyl)-1-imidazolidinyl]carbonyl]amino]benzene-acetic acid | [3S(R*)]-2-oxo-3-[[[[2-oxo-3-(phenylmethyl)-1-imidazolidinyl]carbonyl]amino]phenylacetyl]-amino]-1-azetidinyl sulfate |
| 60. | (Z)-α-(methoxyimino)-2-furanacetic acid | [3S(Z)]-3-[[(2-furanyl)(methoxyimino)acetyl]-amino]-2-oxo-1-azetidinyl sulfate |
| 61. | (R)-α-[[[3-[[(dimethylamino)methylene]amino]-2-oxo-1-imidazolidinyl-carbonyl]amino]benzeneacetic acid | [3S(R*)]-3-[[[[3-[[(dimethylamino)methylene]-amino]-2-oxo-1-imidazolidinyl]carbonyl]amino]-phenylacetyl]amino]-2-oxo-1-azetidinyl sulfate |
| 62. | (R)-α-[[(3-ethyl-2-oxo-1-imidazolidinyl)carbonyl]amino]benzeneacetic acid | [3S(R*)]-3-[[[[(3-ethyl-2-oxo-1-imidazolidinyl)]-carbonyl]amino]phenylacetyl]amino]-2-oxo-1-azetidinyl sulfate |
| 63. | (R)-α-[[[[[(4-methoxyphenyl)methoxy]-carbonyl]amino]acetyl]amino]benzene-acetic acid | [3S(R*)]-3-[[[[[[(4-methoxyphenyl)methoxy]-carbonyl]amino]acetyl]amino]phenylacetyl]-amino]-2-oxo-1-azetidinyl sulfate |
| 64. | (R)-α-[[[2-oxo-3-[[(phenylmethoxy)-carbonyl]amino]-1-imidazolidinyl]-carbonyl amino benzeneacetic acid | [3S(R*)]-2-oxo-3-[[[[2-oxo-3-[[(phenylmethoxy-carbonyl]amino]-1-imidazolidinyl]carbonyl]amino]-phenylacetyl]amino]-1-azetidinyl sulfate |
| 65. | (Z)-2-amino-α-[(2-amino-1,1-dimethyl-2-oxoethoxy)imino]-4-thiazoleacetic acid | [3S(Z)]-3-[[[(2-amino-1,1-dimethyl-2-oxoethoxy)-imino](2-amino-4-thiazolyl)actyl]amino]-2-oxo-1-azetidinyl sulfate |
| 66. | (R)-α-[[[4-(1-methylethyl)-2,3-dioxo-1-piperazinyl]carbonyl]amino]-4-hydroxybenzeneacetic acid | [3S(R*)]-3-[[[[4-(1-methylethyl)-2,3-dioxo-1-piperazinyl]carbonyl]amino](4-hydroxyphenyl)acetyl]amino]-2-oxo-1-azetidinyl sulfate |
| 67. | (R)-α-[[[3-(1-methylethyl)-2-oxo-1-imidazolidinyl]carbonyl]amino]-benzeneacetic acid | [3S(R*)]-3-[[[[3-methylethyl)-2-oxo-1-imidazolidinyl]carbonyl]amino]phenylacetyl]-amino]-2-oxo-1-azetidinyl sulfate |
| 68. | (Z)-2-amino-α-[[2-(diphenylmethoxy)-1-methyl-2-oxoethoxy]imino]-4-thiazoleacetic acid | [3S(Z)]-3-[[(2-amino-4-thiazolyl)[[2-diphenyl-methoxy)-1-methyl-2-oxoethoxy]imino]acetyl]-amino]-2-oxo-1-azetidinyl sulfate |
| 69. | 5-methyl-3-phenyl-4-isoxazolecarboxylic acid | (S)-3-[[(5-methyl-3-phenyl-4-isoxazolyl)-carbonyl]amino]-2-oxo-1-azetidinyl sulfate |

EXAMPLE 70

2-Oxo-3-methoxy-3-[(phenylacetyl)amino]-1-azetidinyl sulfate, pyridine salt (A)

3-Methoxy-3-[(phenylacetyl)amino]-1-[(phenylmethyl)oxy]-2-azetidinone

To a solution of (S)-3-[(phenylacetyl)amino]-1-[(phenylmethyl)oxy]-2-azetidinone (1mM; see example 4B) in freshly distilled tetrahydrofuran (10 ml) at −78° C. is added via syringe a solution of lithium methoxide (3mM) in dry methanol (5 ml). After 5 minutes, t-butyl hypochlorite (130 μl) is added and the mixture is stirred at −78° C. for 30 minutes. The reaction mixture is poured into 0.5 M monobasic potassium phosphate buffer and extracted with two 100 ml portions of methylene chloride. The combined organic extracts are dried over sodium sulfate and concentrated to an oily residue. The title compound is isolated by column chromatography as a racemate.

(B)

2-Oxo-3-methoxy-3-[(phenylacetyl)amino]-1-azetidinyl sulfate, pyridine salt

Following the hydrogenolysis and sulfation procedures described in example 4, parts C and D, but utilizing 3-methoxy-3-[(phenylacetyl)amino]-1-[(phenylmethyl)oxy]-2-azetidinone in place of (S)-3-[(phenylacetyl)amino]-1-[(phenylmethyl)oxy]-2-azetidinone, yields the title compound.

What is claimed is:

1. A β-lactam having the formula

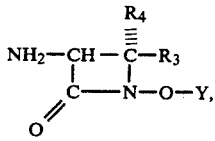

wherein $R_3$ and $R_4$ are the same or different and each is hydrogen or alkyl and Y is benzyl or pivaloyl.

* * * * *